United States Patent [19]
Sioli

[11] Patent Number: 5,986,146
[45] Date of Patent: Nov. 16, 1999

[54] PROCESS AND REACTOR FOR HETEROGENEOUS EXOTHERMIC SYNTHESIS OF FORMALDEHYDE

[75] Inventor: Giancarlo Sioli, Cernobbio, Italy

[73] Assignee: Floriall Holdings Limited, Dublin, Ireland

[21] Appl. No.: 08/930,627

[22] PCT Filed: Apr. 9, 1996

[86] PCT No.: PCT/EP96/01517

§ 371 Date: Dec. 5, 1997

§ 102(e) Date: Dec. 5, 1997

[87] PCT Pub. No.: WO96/32190

PCT Pub. Date: Oct. 17, 1996

[30] Foreign Application Priority Data

Apr. 11, 1995 [CH] Switzerland ............ 1041/95

[51] Int. Cl.$^6$ .................................. C07C 45/29
[52] U.S. Cl. ................. 568/472; 568/448; 568/487; 568/422; 422/196; 29/401.1
[58] Field of Search .................. 568/448, 422, 568/472, 487; 422/196; 29/401.1

[56] References Cited

U.S. PATENT DOCUMENTS

| | | |
|---|---|---|
| 2,504,402 | 4/1950 | Field . |
| 2,512,562 | 6/1950 | Cummings . |
| 4,372,920 | 2/1983 | Zardi ........................ 422/148 |
| 4,755,362 | 7/1988 | Zardi ........................ 422/148 |
| 4,904,453 | 2/1990 | Zardi ........................ 422/148 |
| 4,952,375 | 8/1990 | Zardi ........................ 422/148 |

FOREIGN PATENT DOCUMENTS

| | | |
|---|---|---|
| 3318098 | 11/1984 | Germany . |
| 60-110328 | 6/1985 | Japan . |
| 2055606 | 3/1981 | United Kingdom . |
| 2122102 | 1/1984 | United Kingdom . |

*Primary Examiner*—Shailendra Kumar
*Assistant Examiner*—Sreeni Padmanabhan
*Attorney, Agent, or Firm*—Sughrue, Mion, Zinn, Macpeak & Seas, PLLC

[57] ABSTRACT

A process for the heterogeneous exothermic synthesis of formaldehyde, in particular in a reactor of the type comprising a plurality of adiabatic catalytic beds connected in series, provides the step of feeding to the reactor the methanol necessary for the synthesis distributed in at least two portions, each fed to respective distinct catalytic beds.

9 Claims, 2 Drawing Sheets

PROCESS AND REACTOR FOR HETEROGENEOUS EXOTHERMIC SYNTHESIS OF FORMALDEHYDE

This is the U.S. National stage application of PCT/EP96/01517 filed Apr. 9,1996 now WO 96/32190 published Oct. 17, 1996.

DESCRIPTION

1. Field of Application

The present invention relates to a process for heterogeneous exothermic synthesis of formaldehyde in excess oxygen, in particular in a synthesis reactor of the type comprising a plurality of adiabatic catalytic beds connected in series, with the process comprising the steps of:

feeding gaseous reagents comprising methanol and excess oxygen to a first of said catalytic beds, wherein the methanol fed to the synthesis reactor (7) is distributed in a plurality of portions, a first of which is fed to a first catalytic bed while at least a second one is fed to a distinct catalytic bed disposed downstream of said first catalytic bed;

causing said gaseous reagents to flow across said adiabatic catalytic beds to subject the methanol to partial oxidation.

The present invention also relates to reactors for heterogeneous exothermic synthesis of formaldehyde. In the description given below and in the following claims, the term: 'adiabatic catalytic bed', is understood to mean a bed containing catalyst in which the synthesis reaction takes place at a substantially constant pressure without heat removal.

In the field of heterogeneous exothermic synthesis of formaldehyde, the requirement on the one hand of increasing the productive capacity of the synthesis reactors and on the other hand of reducing the risks of explosion of the gaseous reagents comprising methanol and oxygen in excess, while holding down energy consumption and investment and maintenance costs, is increasingly felt.

2. Prior Art

For the purpose of meeting the above mentioned requirement, tubular reactors with heat removal by passage of a cooling liquid circulating outside the tubes have become increasingly accepted.

This type of reactor consisting of a plurality of small-diameter tubes filled with catalyst is very complicated to construct and has limited production capacity.

In the second half of the nineteen-eighties there was proposed by the Boreskov Institute of Catalysis of Novosibirsk, Russia, the adoption of a formaldehyde synthesis process in which the gaseous reagents comprising methanol and excess oxygen are reacted in a plurality of adiabatic catalytic beds connected in series.

The gaseous reagents cross the catalytic beds with axial flow. Between the outlet from a bed and the inlet to the following bed the gas flow is appropriately cooled by heat exchange in suitable heat exchangers.

The above mentioned process permits provision of reactors of large size and having a production capacity higher than that obtainable with the conventional tubular reactors, since it is possible to increase the reaction space and the flowrate of the gaseous reagents and it is possible to improve the selectivity of the oxidation reaction of the methanol.

If on the one hand this type of solution proves to be advantageous as compared with tubular reactors, on the other hand the production capacity of the synthesis reactor remains limited by the concentration of methanol contained in the gaseous reagents entering the reactor.

As known, this concentration must be held below certain values which generally do not exceed 6%–9% by volume depending on the oxygen concentration, which can vary between 5% and 21% by volume, to avoid the possible formation of explosive or inflammable mixtures with the oxygen.

A relatively low concentration of methanol is also preferable for limiting the amplitude of temperature variations in the catalytic mass. Indeed, at temperatures over 300° C. there is the risk of deterioration of the catalyst with resulting reduction of its useful life and a drastic increase in the undesired secondary reactions which lead to direct degradation of the methanol or of the formaldehyde produced.

In addition, the embodiment of a large synthesis reactor with large gas flowrates of the type developed by the Boreskov Institute of Catalysis involves considerable technical difficulties, high investment costs and high energy consumption.

In US-A-2 504 402, it is also described a process for the heterogeneous exothermic synthesis of formaldehyde in a reactor comprising a plurality of adiabatic catalytic beds connected in series, wherein a stoichiometrical amount of methanol is introduced into each bed.

SUMMARY OF THE INVENTION

The technical problem underlying the present invention is to increase the production capacity of formaldehyde synthesis reactors while reducing the risks of explosion of the gaseous reagents comprising methanol and excess oxygen while holding down energy consumption and investment and maintenance costs.

This problem is solved by a process of the above mentioned type which is characterized in that said first portion is a major portion of the methanol fed to the synthesis reactor.

Thanks to the process according to the present invention, between the outlet from a catalytic bed and the inlet to the following catalytic bed the gaseous reagents are fed with a fluid comprising methanol.

In this manner, instead of introducing into the gas flow fed to the first of the catalytic beds the entirety of the methanol necessary for the reaction, the methanol is advantageously metered into the synthesis gas during its passage through the reactor progressively as the conversion reaction takes place.

By operating in this manner it is possible to control the concentration of methanol in the gas flow entering the catalytic beds. This concentration can thus be held at optimal values which are generally between 6% and 9% by volume, and thus obtain high production capacity of the synthesis reactor without thereby having to increase the risk of explosion of the methanol/oxygen mixture.

Advantageously, the gaseous reagents are made to flow across at least one of the catalytic beds with a substantially radial flow and preferably of centripetal type.

The flow of synthesis gas with substantially radial motion permits uniform distribution of the gas striking the catalytic bed, and this is an important feature for ensuring uniform distribution of temperature and hence high selectivity in the conversion of the methanol to formaldehyde and optimal utilization of the catalytic mass.

In this manner it is possible to obtain a further increase in the production capacity of the synthesis reactor.

Furthermore, thanks to a radial flow of the gaseous reagents across the catalytic beds it is possible to utilize in the best manner the internal volume of the reactor and this helps increase the reaction space and hence production capacity.

Advantageously, the structure of the reactor resulting from this process is technically simpler and more compact with respect to that of the reactor which can be obtained by the process according to the prior art.

In accordance with another aspect of the present invention, the process allows performance of cooling of at least part of a hot gas flow coming from at least one of the catalytic beds by heat exchange in a heat exchanger arranged in the center of the reactor and extending along a longitudinal axis thereof.

In this manner, it is possible to optimize utilization of the internal volume of the reactor to reduce to a minimum the spaces between consecutive catalytic beds. So doing the reaction space inside the synthesis reactor and hence its production capacity is further increased and at the same time the structure of the reactor is made still more compact and simple.

In a preferred embodiment of the process according to the present invention, the oxygen fed to the synthesis reactor is divided in at least two portions, with each being fed to distinct catalytic beds.

Specifically, the present process also calls for the step of injecting into the gas flow coming from at least one of the catalytic beds, a gaseous or liquid flow comprising oxygen.

The intermediate inlet of oxygen into the gas flow traversing the reactor permits achievement of a dual advantage.

On the one hand, it is possible to reduce the oxygen concentration in the reaction gas flow fed to the first catalytic bed to permit increase of the initial methanol concentration while the mixture of the two reagents remains below the explosive limit.

On the other hand, the oxygen thus apportioned in the catalytic beds allows keeping the catalyst constantly in the oxidized state to protect it from possible losses of activity. This phenomenon is generally found at the final step of the oxidation reaction when the oxygen concentration falls below a certain threshold such as for example 3-4% by volume.

In addition, the process according to the present invention comprises advantageously the step of extracting from the reactor at least part of a gas flow coming from at least one of the catalytic beds.

In this manner it is possible to obtain a gaseous formaldehyde flow coming from the outlet of the synthesis reactor substantially free from methanol and suitable for direct employment for the required uses, for example resin production, and one or more intermediate gaseous flows comprising formaldehyde and methanol useful for the direct preparation of aqueous formaldehyde solutions in which the methanol in concentrations of 7–12% acts as a polymerization inhibitor.

In accordance with another aspect of the present invention, there are also made available reactors for heterogeneous exothermic synthesis of formaldehyde of the type recited in claims 10, 15 and 16.

The characteristics and advantages of the present invention are set forth in the description of an embodiment thereof given below by way of non-limiting example with reference to the annexed drawings.

DETAILED DESCRIPTION OF A PREFERRED EMBODIMENT

Figure 1:
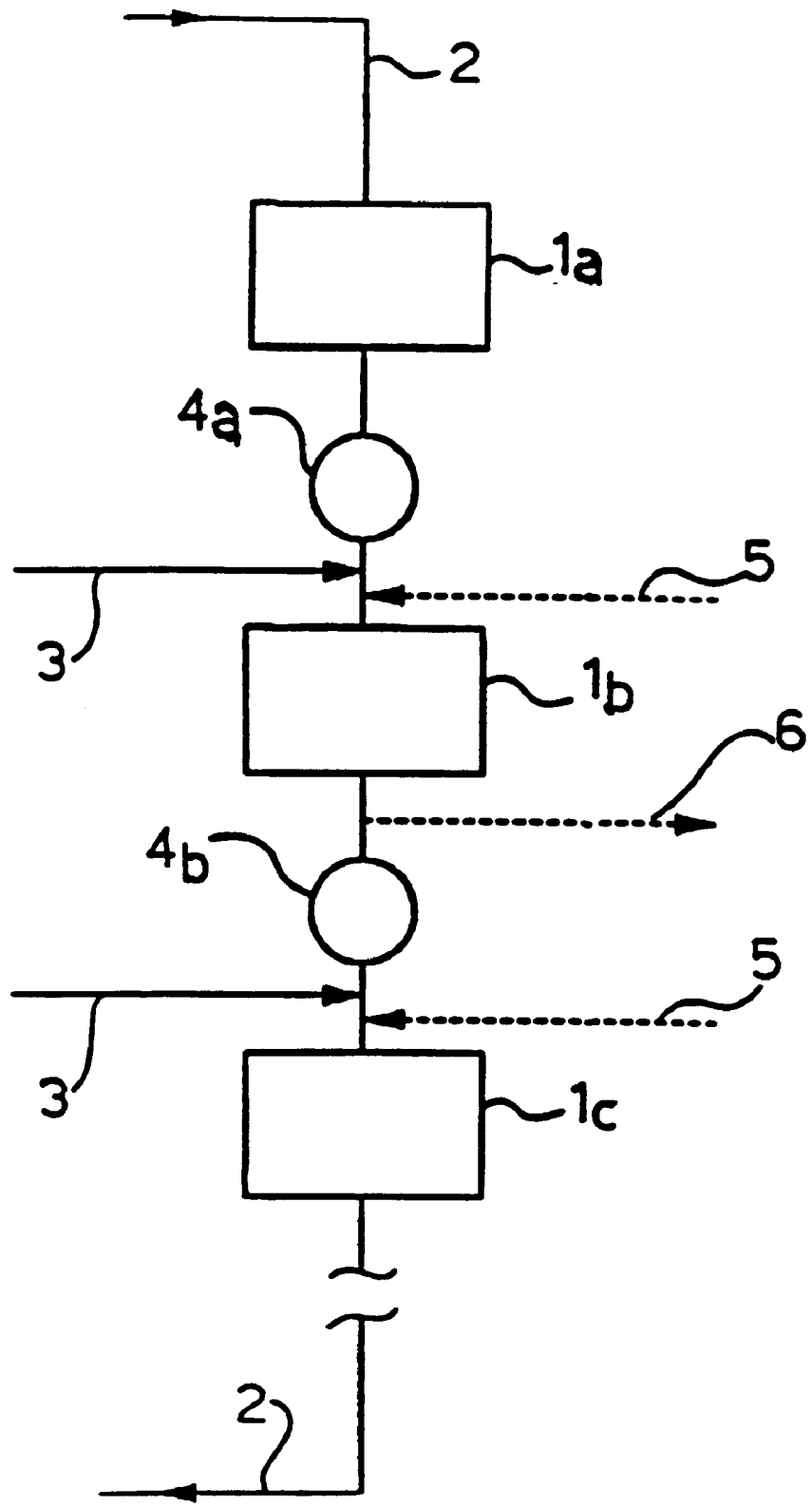
FIG. 1 shows a block diagram of the process according to the present invention for the heterogeneous exothermic synthesis of formaldehyde.

FIG. 1 shows a block diagram illustrating the steps of the process for the heterogeneous exothermic synthesis of formaldehyde at low pressure (1–3 bar absolute) and high temperature (200–350° C.) according to the present invention.

1a–1c represent a plurality of reaction stages which define the adiabatic reaction space where the formaldehyde synthesis takes place.

The reaction stages 1a–1c are crossed by a flow line 2 of the reagent gases comprising methanol and excess oxygen.

Reference number 3 represents flow lines of a liquid or gaseous fluid comprising methanol which are added to the flow line 2 between consecutive reaction stages 1a–1c.

FIG. 1 also shows a plurality of cooling stages 4a–4b for removal of at least part of the heat produced during the synthesis reaction.

The cooling stages 4a–4b can consist of a plurality of heat exchangers arranged between consecutive reaction stages 1a–1c or, advantageously, of a single-heat exchanger.

In accordance with the process according to the present invention, the gaseous reagents are fed through the flow line 2 to a first reaction stage 1a to then flow through the reaction stages 1a–1c, with conversion into formaldehyde of the methanol subjected to partial oxidation.

In accordance with another step of the present invention, the methanol necessary for the synthesis reaction is divided in at least two portions, each fed to respective distinct reaction stages 1a–1c.

In this manner it is possible to control the concentration of methanol fed to the following catalytic stage, which is kept at the desired optimal level to thus increase total production of formaldehyde obtained in the synthesis reactor.

Advantageously, the methanol concentration in the synthesis gas can be held considerably below the explosion limit without thereby having to limit the productivity of the reactor.

FIG. 1 also shows (in broken lines) the flow lines 5 and 6 which are respectively for addition to the flow 2 of a gaseous or liquid flow comprising oxygen and removal from the reactor 1 of a gaseous flow comprising formaldehyde and methanol.

In accordance with a first embodiment, the process according to the present invention also provides the step of enriching the gaseous flow traversing the reactor with a flow comprising oxygen, for example air. In this manner it is possible to perform an optimal metering of the oxygen into the gaseous flow 2 traversing the reactor to thus make possible an increase both of the total quantity of methanol fed to the reactor and of the initial concentration of methanol in the synthesis gas fed to the first catalytic bed. In addition, there is obtained a constant oxidation of the catalyst contained in the reaction stages 1a–1c.

As an alternative, the oxygen can be fed into the same fluid comprising methanol added to the gaseous flow passing through the synthesis reactor. In this case, in FIG. 1, the flow line 5 corresponds to the flow line 3.

The methanol and/or oxygen fed to the synthesis gas in gaseous form have preferably a temperature between 70 and 250° C. and between 0 and 250° C. respectively. Advantageously, the methanol and/or oxygen are fed separately to the synthesis gas in liquid form in such a manner as to perform the auxiliary function of heat removal of the hot gas flow 2 coming from a reaction stage, to cool it.

The presence of this cooling permits reduction or even elimination of the cooling stages 4a–4b.

In accordance with another embodiment, the present process provides the step of extracting the formaldehyde progressively as it is produced in the reaction stages 1a–1c.

Thanks to this step of the process according to the invention, it is possible to obtain a gas flow 2 coming out of the synthesis reactor 1 substantially free of methanol, and gas flows 6 coming from intermediate zones of the reactor and comprising formaldehyde and methanol useful for the direct preparation of stabilized aqueous formaldehyde solutions.

Advantageously the step of addition of a flow comprising oxygen and the step of intermediate extraction of a flow comprising formaldehyde are carried out within the same synthesis process, downstream of one or more reaction stages.

Figure 2:
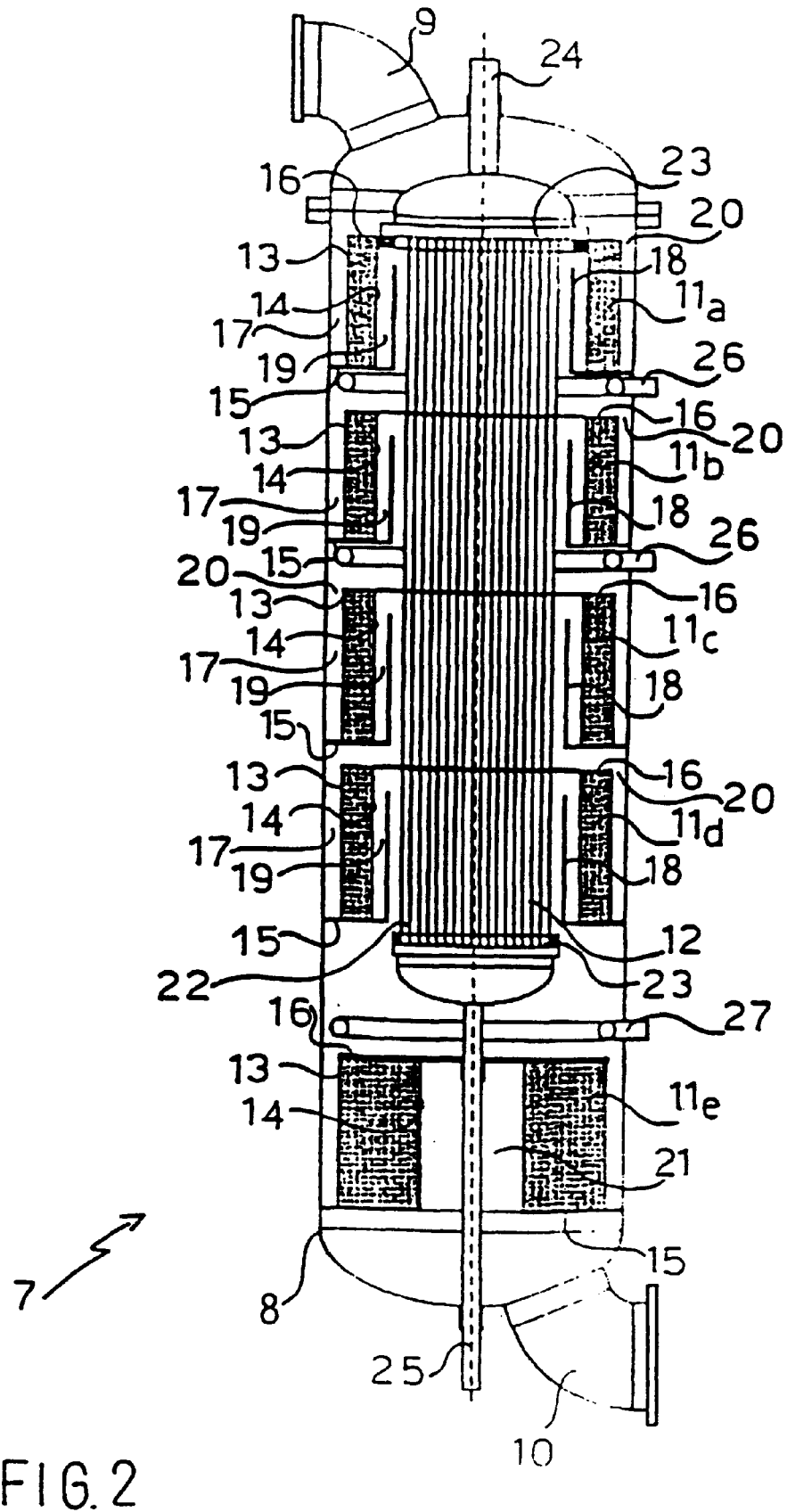
FIG. 2 shows a longitudinal cross section view of a reactor for heterogeneous exothermic synthesis of the formaldehyde according to a preferred embodiment of the present invention.

With reference to FIG. 2, a reactor 7 for the heterogeneous exothermic synthesis of the formaldehyde at low pressure (1–3 bar absolute) and high temperature (200° C. –350° C.) comprises a vertical tubular shell 8 equipped at its ends with openings 9 and 10 for input of the gaseous reagents appropriately preheated and outlet of the reaction products respectively.

The reagents pass through the reactor 7 in the form of a gaseous phase comprising methanol and excess oxygen.

In the shell 8 are supported in mutually spaced relationship a plurality of superimposed annular catalytic beds 11a–11e and a heat exchanger 12 arranged in the center of the reactor 7 and extending along its longitudinal axis.

The catalytic beds 11a–11e are filled with granular catalyst of the type with a base of Fe—Mo, for example of ferric molybdate with possible additions of elements such as for example Mn, Cr, Ti or Co.

In the example of FIG. 2, the catalytic beds 11a–11e comprise opposing gas permeable side walls 13 and 14 delimited below and above by an annular bottom 15 impermeable to the gas and an annular cover 16 impermeable to the gas respectively.

In accordance with a particularly advantageous feature of the process according to the present invention, the gaseous reagents comprising methanol and excess oxygen are made to flow across at least one of the catalytic beds 11a–11e with a substantially radial flow.

In this manner, the catalytic mass contained in the beds is struck uniformly by the gas flows to obtain uniform temperature distribution and hence high selectivity in the conversion of methanol to formaldehyde and optimal utilization of the catalytic mass, with the advantage of an increase in the production capacity of the synthesis reactor.

In a further embodiment of the present process (not shown) the gaseous flow crossing the catalytic beds could be of axial-radial type. In this case the top cover 16 of the catalytic beds 11a–11e would not be used or would be made gas permeable.

As shown in FIG. 2, the bottom 15 extends at one end to the internal wall of the shell 8, with which it defines a hollow space 17 for gas inlet to the catalytic beds 11a–11e.

In some of the catalytic beds 11a–11d, for example catalytic bed 11b, the bottom 15 extends also to an annular baffle 18 arranged between said catalytic bed 11b and the heat exchanger 12. There is thus defined a hollow space 19 for outlet of gas from the catalytic bed 11b, in fluid communication, through the opening 20, with the heat exchanger 12 and the hollow space 17 for gas inlet of the following catalytic bed 11c.

At the outlet from the catalytic bed 11e, there is provided a chamber 21 for collection of the reaction products in fluid communication with the opening 10 for their expulsion from the reactor 7.

Thanks to this particular configuration of the reactor of FIG. 2, it is possible to carry out the process according to the present invention with a step in which the synthesis gas is made to flow across the catalytic beds 11a–11e with a substantially radial flow of the centripetal type from the outside towards the inside of the reactor 7.

The synthesis gas added to the reactor 7 through the opening 9 for gas inlet flows in a first hollow space 17 and crosses radially the first catalytic bed 11a to then collect in the hollow space 19 from which it is made to pass through the opening 20 to the hollow space 17 for gas inlet of the following catalytic bed 11b. The synthesis gas flows in a similar manner through the remaining catalytic beds 11b–11e to then collect in the chamber 20 and exit from the reactor 7 through the opening 10 for gas outlet.

The oxidation reaction of the methanol is conducted in the catalytic beds 11a–11e by successive stages in series, in each of these the degree of conversion is limited to values preferably not higher than 25% of the total quantity of methanol fed to the synthesis reactor 7.

This control of the degree of conversion of the methanol in the individual catalytic beds is advantageously obtained by appropriately limiting the volume of catalyst of each bed.

The synthesis reaction in the catalytic beds 11a–11e takes place under adiabatic conditions without removal of the heat developed during the passage of the gaseous reagents across the catalytic mass. The reaction heat will then go to increase the temperature of the synthesis gas coming from each of the catalytic beds 11a–11e.

The temperature increase of the gaseous mixture in the catalytic bed is proportionate to the quantity of oxidized methanol, which is therefore held within values such as to not cause development in the catalytic bed of excessively high temperatures, for example higher than 330–350° C., which would be detrimental to the good progress of the reaction of conversion of the methanol into formaldehyde and to useful life of the catalyst.

Between a catalytic bed 11a–11d and the next 11b–11e, the gaseous reagents are made to pass through the heat exchanger 12 on the shell side and are cooled by means of heat exchange to a temperature such that the oxidation reaction can resume spontaneously when the gas comprising methanol and oxygen comes into contact with the catalyst of the following bed 11b–11e; generally this temperature is between 200 and 250° C.

The heat exchanger 12 is advantageously of the tube nest type comprising a plurality of tubes 22 held in fixed position by two tube plates 23 arranged at their ends.

The cooling fluid which removes the reaction heat is fed into the reactor 7 through the inlet duct 25 in fluid communication with the lower tube plate 23, and thence made to pass internally to the tubes 22 to then exit from the reactor 7 appropriately heated through the outlet duct 24 in fluid communication with the upper tube plate 23.

Generally, the cooling fluid consists of a diathermic mineral or synthetic oil, a mixture of melted salts, an evaporating liquid such as Dowthern or a gas. Preferably superheated or evaporating water is used so as to produce steam which is useful in an industrial plant.

By providing the tube nest with tubes 22 of the so-called low-finned type, the dimensions of the heat exchanger 12 can be considerably reduced providing the advantage of greater reaction space and hence an increase in the productive capacity of the synthesis reactor.

As shown in FIG. 2, the gaseous flow coming from the last catalytic bed 11e is not cooled but is made available at its maximum temperature for the purpose of preheating the fresh gas to be fed to the first catalytic bed 11a. The heat exchange between the hot gaseous flow and the cold gaseous reagents can take place in a heat exchanger or a preheater, of known type and therefore not shown, arranged outside the shell 8 or inside it.

As an alternative, inside the reactor of FIG. 2 there can be arranged a single heat exchanger 12 extending centrally along all the catalytic beds 11a–11e for cooling of the hot gas flow emerging therefrom.

In another embodiment (not shown), the heat exchanger can be arranged outside the shell 8. In this case, the flow of the synthesis gas across the catalytic beds will be preferably of the radial centrifugal type from the interior towards the exterior of the reactor 7.

Reference numbers 26 and 27 indicate toroidal distributors for inlet to the underlying catalytic beds of a liquid or gaseous flow comprising methanol or oxygen respectively.

The functional characteristics of these distributors and the associated advantages resulting from the intermediate inlet of methanol and oxygen were described above with reference to the flow lines 3 and 5 of FIG. 1.

The distributors 26 and 27 are arranged between consecutive catalytic beds near the hollow space 17 for gas inlet.

In accordance with the embodiment of FIG. 2, at the inlet to the second and third catalytic beds 11b and 11c there is advantageously injected a fluid comprising methanol, while at the inlet to the last catalytic bed 11e is injected a fluid comprising oxygen.

The number and arrangement of the distributors 26 and 27 in the shell 8 can in any case be freely varied depending on the specific requirements of the synthesis reactor.

The liquid or gaseous flow fed to the catalytic beds 11b, 11c has advantageously a methanol content between 6% and 8 % by volume.

In accordance with a further embodiment of the present invention (not shown), between at least two consecutive catalytic beds is also provided a gas outlet duct for extraction from the reactor 7 of part of the gaseous flow crossing the catalytic beds and comprising formaldehyde as described above with reference to the flow line 6 of FIG. 1.

The intermediate formaldehyde extraction, just as the distribution in the catalytic beds of portions of methanol and/or oxygen can be performed as an alternative in special equipment arranged outside the reactor 7.

In accordance with another embodiment of the reactor of FIG. 2, part of the gaseous flow coming from a catalytic bed 11a–11d is advantageously conveyed through a bypass duct (not shown) directly into the following catalytic bed 11b–11e without passing through the heat exchanger 12.

In this manner it is possible to influence in a controlled manner the temperature of the gaseous flow fed to the following catalytic bed 11b–11e.

Advantageously, the reactor represented in the example of FIG. 2 with a plurality of radial catalytic beds and a single central heat exchanger permits obtaining at the same time a very compact and technically simple structure which would be very economical and with optimal utilization of the internal volume of the reactor, with the advantage of an increase in the reaction space and hence in productive capacity.

In addition, the fact of dividing the reaction space into a plurality of catalytic beds connected in series allows optimal control of the progress of the oxidative reaction of the methanol permitting minimization of the undesirable secondary reactions and extending the useful life of the catalyst.

By changing the number of the catalytic beds arranged in the reactor of FIG. 2 and the volume of the catalyst contained therein, it is possible to control the reaction while it is taking place to aid for -example conversion of the methanol even where the reduced concentration of the reagents would tend to slow it.

Advantageously, the number of the catalytic beds is generally between 4 and 10. Particularly satisfactory results were obtained with reactors having 5 to 6 catalytic beds.

In particular it was found that with a reactor with 5 catalytic beds of the type exemplified in FIG. 2 it is possible to limit the degree of conversion of the methanol in each catalytic bed to approximately 20% of the total quantity of methanol fed to the synthesis reactor. In this manner it is possible to obtain in the beds an optimal reaction temperature between 220 and 310° C., which is less than that for example of a reactor having four catalytic beds where the degree of conversion in each bed is approximately 25%, with a resulting increase in the selectivity and hence in the productive capacity of the reactor.

Lastly, thanks to the special simple and compact structure of the reactor according to the present invention, the operations of maintenance and of loading and unloading of the catalytic mass prove to be considerably simpler and faster as compared with the prior art.

In the following examples comparison is made for indicative and non-limiting purposes of the production capacity obtained from some embodiments of a reactor according to the present invention and a reactor according to the prior art.

EXAMPLE 1

The production capacity of a reactor according to the present invention with intermediate inlet of methanol is compared with the production capacity of a reactor of conventional type with axial catalytic beds.

Inside the two reactors examined are arranged in mutually spaced relationship four adiabatic catalytic beds.

The reactors have the following dimensions.

| | |
|---|---|
| Internal diameter of shell: | 3.0 m |
| Total reactor height: | 20.0 m |
| Internal volume of reactor: | 140 m$^3$ |
| Catalyst volume of 1st bed: | 1300 l |
| Catalyst volume of 2nd bed: | 1400 l |
| Catalyst volume of 3rd bed: | 1600 l |
| Catalyst volume of 4th bed: | 2800 l |

-continued

Operating conditions are as follows.

| | |
|---|---|
| Average pressure: | 1.3 ata |
| Temperature at catalytic bed inlet: | 230° C. |
| Temperature at catalytic bed outlet: | 330° C. |
| Methanol concentration (1st bed inlet): | 6.5% by vol |
| Oxygen concentration (1st bed inlet): | 8.0% by vol |

In the case of the reactor according to the prior art the total quantity of methanol fed to the reactor is equivalent to the total quantity of methanol fed to the first catalytic bed which is 3130 kg/h.

In the reactor according to the present invention, in addition to the 3130 kg/h fed to the first catalytic bed there are advantageously fed an additional 750 kg/h of methanol to the second bed for a total quantity of methanol of 3835 kg/h.

The methanol is fed to the two reactors in gaseous phase and crosses the catalytic beds with axial flow.

The quantity of formaldehyde produced by the two reactors is shown below.

| | |
|---|---|
| Conventional reactor: | 2720 kg/h |
| Reactor according to the invention: | 3360 kg/h |

An increase of 640 kg/h of formaldehyde produced by the reactor according to the present invention corresponds to an increase in the production capacity of 23.5% which is a very considerable result if considering also a reduction in energy consumption per unit of product of approximately 24%.

EXAMPLE 2

The production capacity of a reactor of the type shown in FIG. 2 is compared with the production capacity of a conventional reactor with axial catalytic beds.

The data for the reactor according to the prior art correspond to those indicated in Example 1 with reference to the conventional reactor.

The reactor according to the present invention comprises instead five catalytic beds crossed radially by the synthesis gas.

The total volume of catalyst in the synthesis reactor amounts in this case to 8450 liters while the temperature at the output of the catalytic beds is approximately 310° C.

The other data for the operating conditions correspond to those indicated in Example 1 with reference to the reactor according to the invention.

The quantity of formaldehyde produced by this reactor is 3430 kg/h.

Thanks to the particular structure of the reactor according to the present invention, the production capacity is further increased by 1.9% with respect to Example 1 with a reduction of the volume of the reactor of approximately three times.

EXAMPLE 3

The reactor according to the present invention described in Example 2 comprises additionally a gas distributor for the addition of air, arranged upstream of the fifth catalytic bed as shown in FIG. 2.

The quantity of air fed to the last catalytic bed is 4000 $Nm^3/h$.

With respect to Example 2, the addition of a gaseous flow comprising oxygen permits practically complete conversion of the methanol, which results in an increase in the quantity of formaldehyde produced (3470 kg/h instead of 3369 kg/h), and a reduction in the volume of catalyst in the last catalytic bed of 12%.

I claim:

1. A process for the heterogeneous exothermic synthesis of formaldehyde in a reactor comprising a plurality of adiabatic catalytic beds connected in series, said process comprising the steps of:

feeding gaseous reagents comprising methanol and excess oxygen to said reactor, wherein methanol fed to the synthesis reactor is distributed into a pluralit of portions, a first portion of said methanol being fed to a first catalytic bed while at least a second portion of said methanol is fed to a distinct catalytic bed disposed downstream of said first catalytic bed; and partially oxidizing said methanol by flowing said methanol across said adiabatic catalytic beds;

wherein said first portion is a major portion of said methanol fed to the synthesis reactor.

2. A process according to claim 1, wherein said first portion is about 82% of the menthanol fed to said reactor.

3. A process according to claim 1, wherein said gaseous reagents flow across at least one of said catalytic beds with a substantially radial flow.

4. A process according to claim 3, wherein said gaseous reagents flow across at least one of said catalytic beds (11a–11e) with axial-radial flow.

5. A process according to claim 3, wherein said substantially radial flow is in a centripetal direction.

6. A process according to claim 5, further comprising the step of cooling of at least part of a hot gas flow coming from said at least one of the catalytic beds by heat exchange in a heat exchanger arranged centrally to said reactor and extending along a longitudinal axis thereof.

7. A process according to claim 1, wherein said oxygen fed to said synthesis reactor is distributed into at least two portions, each portion being fed to different catalytic beds.

8. A process according to claim 7, further comprising the step of:

injecting into a gaseous flow coming from at least one of said catalytic beds, a gaseous or liquid flow comprising oxygen.

9. A process according to claim 1, further comprising the step of:

extracting from said reactor at least part of a gas flow coming from at least one of said catalytic beds.

* * * * *